United States Patent [19] [11] Patent Number: 5,090,401
Schwieker [45] Date of Patent: Feb. 25, 1992

[54] METHOD OF POSITIONING A PATIENT ARRANGED ON A TABLE TOP OF A PATIENT TABLE, AND APPARATUS FOR PERFORMING THE METHOD

[75] Inventor: Horst H. Schwieker, Hamburg, Fed. Rep. of Germany

[73] Assignee: U.S. Philips Corporation, New York, N.Y.

[21] Appl. No.: 640,516

[22] Filed: Jan. 11, 1991

Related U.S. Application Data

[63] Continuation of Ser. No. 400,185, Aug. 29, 1989, abandoned.

[30] Foreign Application Priority Data

Sep. 6, 1988 [DE] Fed. Rep. of Germany ....... 3830183

[51] Int. Cl.$^5$ ............................................. A61B 17/22
[52] U.S. Cl. ................... 128/24 EL; 128/653.1; 378/20; 378/205
[58] Field of Search ......... 128/653 R, 24 EL, 660.03; 378/20, 68, 69, 205

[56] References Cited

U.S. PATENT DOCUMENTS 3,991,310 11/1976 Morrison .......................... 378/205
4,633,494 12/1986 Klausz .
4,730,351 3/1988 Heumann .......................... 378/20
4,764,944 8/1988 Finlayson ......................... 378/20
4,796,613 1/1989 Heumann et al. ............... 128/24 EL
4,811,725 3/1989 Grasser ........................... 128/24 EL
4,829,986 5/1989 Eichler et al. .
4,877,017 10/1989 Hahn et al. ..................... 128/24 EL

FOREIGN PATENT DOCUMENTS 0257429 8/1987 European Pat. Off. .
0286170 10/1988 European Pat. Off. ........ 128/24 EL Primary Examiner—Ruth S. Smith
Attorney, Agent, or Firm—William Squire

[57] ABSTRACT

A method and apparatus for positioning a patient arranged on the top of a patient table wherein two X-ray images are formed from different perspectives after which they are stored. After the first X-ray image, the table top is displaced in two mutually perpendicular directions and a marker which is electronically superposed on the X-ray image on a monitor is also shifted until it is situated in the region in the X-ray image which is to be positioned. After a second X-ray exposure this operation is repeated. The shift of the marker in the different directions on the monitor or the displacement of the table top in the three spatial directions are not mutually independent but are derived from the value obtained at the end of the first positioning operation.

8 Claims, 3 Drawing Sheets

METHOD OF POSITIONING A PATIENT ARRANGED ON A TABLE TOP OF A PATIENT TABLE, AND APPARATUS FOR PERFORMING THE METHOD

This is a continuation of application Ser. No. 400,185, filed Aug. 29, 1989 now abandoned.

BACKGROUND OF THE INVENTION

The invention relates to a method of positioning a patient arranged on the top of a patient table, where a first X-ray image is formed with the central ray extending in a first direction, which image is electronically stored. The table top is then displaced in a first direction and a second direction which is perpendicular thereto during a first positioning operation, the X-ray image and an electronic marker superposed thereon being shifted relative to one another on a monitor in accordance with the path of travel. The invention also relates to an apparatus for performing the method.

For many examinations and treatments in the medical field it is necessary to bring a given region of a patient in an exactly defined position. For example, for the crushing of renal calculi the patient must be moved in space so that the concrement, i.e. the renal calculus, is positioned exactly in the focus of a shock-wave generator for crushing concrements.

It is known that in apparatus of this kind the location and positioning can be performed by means of an X-ray fluoroscopy device. The table top is then displaced under fluoroscopic control from different perspectives until the image of the renal calculus is situated in a given position within the fluoroscopic image, for example in the center of the image, the position being made visible preferably by means of a suitable electronic marker, for example by means of cross-hairs. It is a drawback that during such a positioning operation not only the patient but also the operator is exposed to a comparatively large radiation dose, because fluoroscopy is continued until the renal calculus is situated in the desired position.

In the method and apparatus described in the preamble, being known from EP-OS 160 583, the radiation dose is reduced because positioning is performed by means of a single X-ray image for which the X-rays need only be briefly switched on. However, accurate positioning can then be realized only if the concrement happens to be already present in the plane parallel to the table top in which its desired position is situated. Otherwise accurate position is not possible, that is to say not in the longitudinal and the transverse direction of the table top either, because an X-ray image is a central projection.

SUMMARY OF THE INVENTION

It is the object of the present invention to enable accurate positioning of a patient using a lower radiation dose.

On the basis of a method of the kind set forth this object is achieved in accordance with the invention in that from a second perspective a second image is formed and electronically stored, the table top subsequently being displaced in a third direction perpendicular to the first two directions, during a second positioning operation, the displacement in the third direction being automatically linked to a displacement in the first and the second direction so that the path of travel in the first and the second direction is proportional to the product of the path of travel in the third direction and the path of travel in the first and the second direction during the first positioning operation, the relationship between the relative displacement of the marker and the table top displacement being calculated from the paths of travels after the first exposure, said displacements being performed as calculated.

Thus, in accordance with the invention two X-ray images are formed from different perspective and two positioning operations are performed. After the first positioning operation the region of the patient which is to be moved to a defined position, for example a renal calculus, is situated on a straight line which extends through this position and parallel to the projection direction of the renal calculus. When the paths of travel in the first and the second direction are coupled to the path of travel in the third direction so that the paths of travel in the first two directions are proportional to the product of the path of travel in the third direction and the paths of travel in the first and the second direction at the end of the first positioning operation, it can be achieved that the renal calculus is moved exactly along this straight line. Because the relative displacement of the marker and the table top displacement is calculated at the same time, it is ensured that the electronic marker in the X-ray image coincides with the image of the renal calculus at the instant at which the renal calculus reaches the desired position, so that the operator knows that the positioning operation can be terminated.

It is an advantage of the invention that the patient is already comparatively near to the desired position after the first positioning operation. Consequently non-linearities such as may be caused inter alia by the curvature of the entrance screen of the image intensifier used to form the X-ray images can have only a limited effect on the accuracy of positioning. A further advantage consists in that the displacement of the table top and the electronic marker in the X-ray image can be controlled via a control unit which is anyhow required for controlling the displacement of the table top.

The different perspectives in which the X-ray images are formed are realized in a preferred embodiment of the invention in that the first and the second image are formed with a central ray extending in different directions. To this end, the X-ray imaging system must be constructed so as to be pivotable.

This condition can be dispensed with in a further embodiment of the invention in that the two X-ray images are formed using the same direction of the central ray, and in that subsequent to the first positioning operation and prior to the second X-ray exposure the table top is displaced in the first or the second direction over a defined distance. Even though the central beam has the same direction during both exposures, the concrement will appear in different perspectives because of the displacement after the first positioning operation. However, the accuracy of this method is not quite as high as that of the previously described method.

BRIEF DESCRIPTION OF THE DRAWING

The invention will be described in detail hereinafter with reference to the drawings. Therein.

DETAILED DESCRIPTION OF THE PREFERRED EMBODIMENTS

Figure 1:
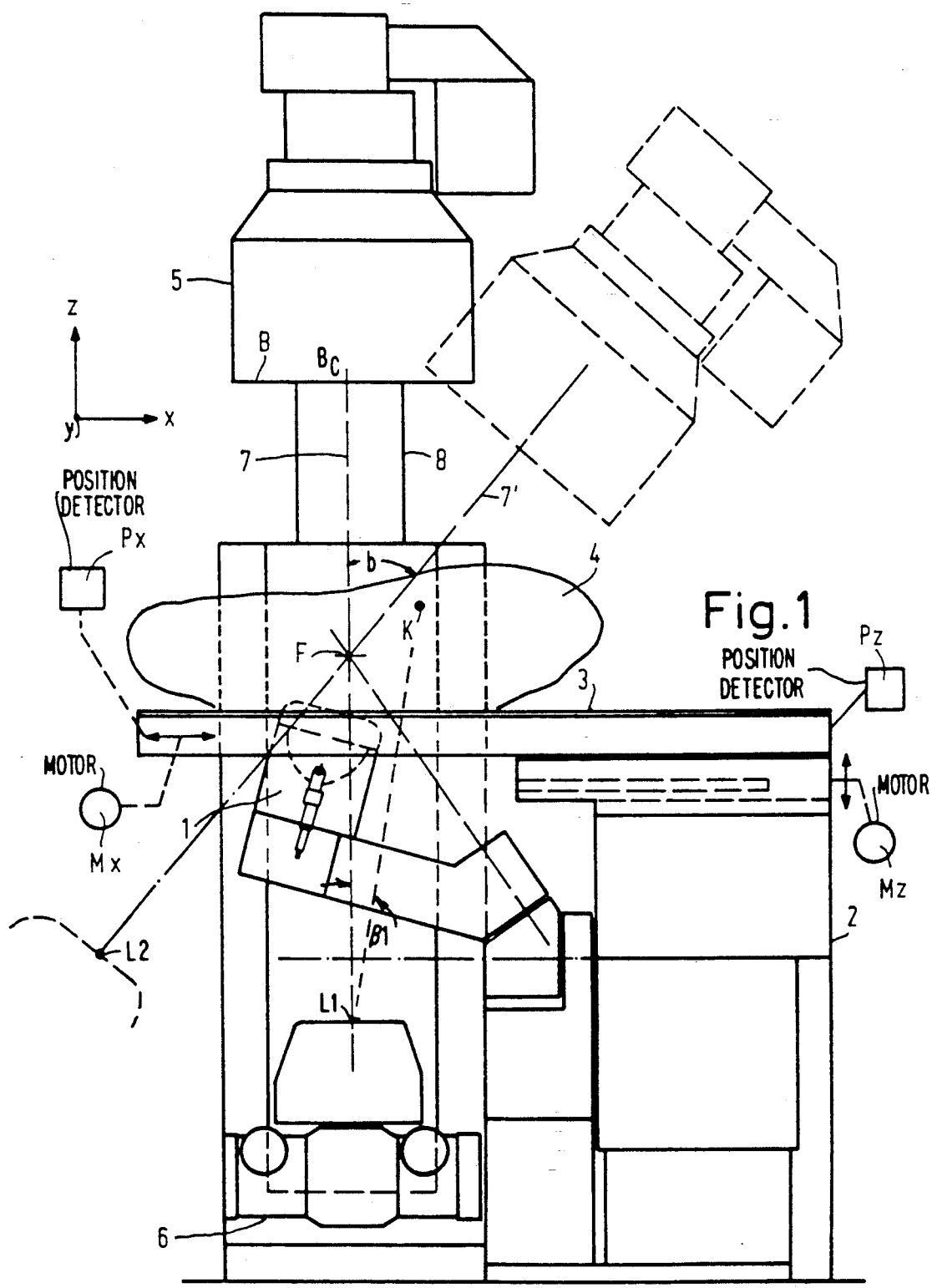
FIG. 1 shows an X-ray apparatus for carrying out the invention.

FIG. 1 shows a lithotriptor apparatus enabling the location of concrements (renal calculi), their positioning in the focus of a shockwave generator, and their crushing. The apparatus comprises a shockwave generator 1 which is capable of generating a shock wave focussed to focus F. The patient 4 to be examined is arranged on a patient table 2 which comprises a table top 3 which can be displaced in the x-direction (i.e. horizontally with respect to the plane of drawing of FIG. 1), in the y direction (perpendicular to the plane of drawing), and in the z direction (vertically). The table top must be displaced so that the concrement K within the body of the patient 4 is situated in the focus F of the shockwave generator 1.

For the displacement of the table top in the x direction there is provided a drive motor Mx which forms part of a control circuit, together with a position detector Px which measures the position in the x direction. There is also provided a drive motor Mz for displacing the table top 3 in the z direction and an associated position detector Pz. The drive motor My and the position detector Py for the y direction are not shown in FIG. 1.

The locating and the positioning are performed by means of an X-ray imaging system which comprises an image converter 5 in the form of an image intensifier and a radiation source in the form of an X-ray source 6. The radiation beam emitted by the X-ray source 6 is directed onto the entrance face B of the image intensifier 5. The central ray 7, linking the center Bc of the image intensifier to the focal spot F, extends vertically in the initial position. The shockwave generator is moved out of the beam path during locating or positioning.

The X-ray source 6 and the image intensifier 5 are connected to one another via a supporting arm 8 which is pivotable about an axis which extends through the focus F in the y direction. FIG. 1 also shows the image intensifier 5 in a pivoted position, denoted by broken lines, in which the central beam 7' intersects the vertical central beam 7 in the focus F.

Figure 2:
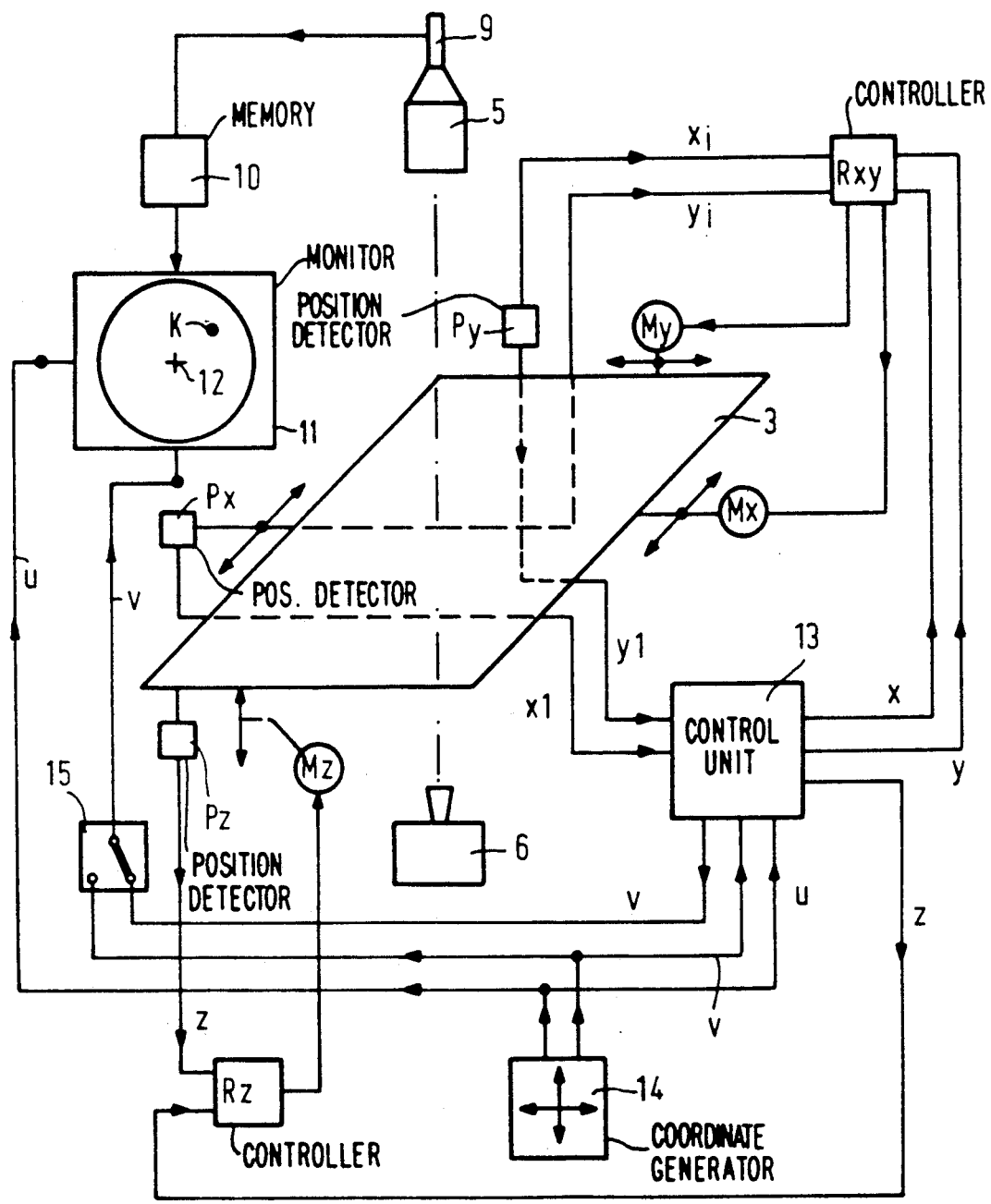
FIG. 2 shows a circuit diagram of the table top control system of such an apparatus.

As appears from FIG. 2, a television camera 9 is connected to the exit of the image intensifier 5, the video signal of the camera being stored in a memory 10 after an X-ray exposure. The stored X-ray image is displayed on a monitor 11. A marker, for example cross-hairs 12, represents the focus F and is electronically superposed on the X-ray image. When the table top is displaced, the X-ray image and the cross-hairs 12 are shifted relative to one another on the monitor. This relative shift can be realized in that the X-ray image is shifted while the cross-hairs 12 remain stationary. However, it is more attractive to keep the X-ray image on the monitor stationary and to shift only the cross-hairs. The cross-hairs 12 thus move towards the concrement K in the X-ray image, as the concrement K in the patient moves towards the focus F. Two signals u and v are applied to the monitor in order to shift the cross-hairs 12 within the X-ray image.

As has already been stated, the drive motors Mx, My and Mz for the displacement of the table top in the x, y and z directions form control circuits, in conjunction with the associated position detectors Px, Py and Pz as well as controllers Rxy and Rz, which circuits determine the position of the table top. The variables x, y and z for these control circuits are generated by a control unit 13 which calculates the signals x, y and z from the signals u and v. Unit 13 also stores the paths of travel x1 and y1 obtained at the end of the first positioning operation in the x direction and the y direction. The signals u and v which represent the coordinates of the cross hairs 12 are supplied by a coordinate generator 14.

The table top is displaced as follows in order to position the concrement K in the focus F of the shockwave generator 1.

First of all a first X-ray image is formed during which the X-ray imaging device 5, 6 occupies the position denoted by non-interrupted lines in FIG. 1. The central ray 7 extends in the vertical direction, perpendicularly to the table top 3. The X-ray image is stored in the memory 10 and is displayed on the monitor 11. The table top is then displaced in the x direction and the y direction, and the cross-hairs 12 are shifted on the display screen 11 in proportion to the movement of the patient on the table top.

Figure 3:
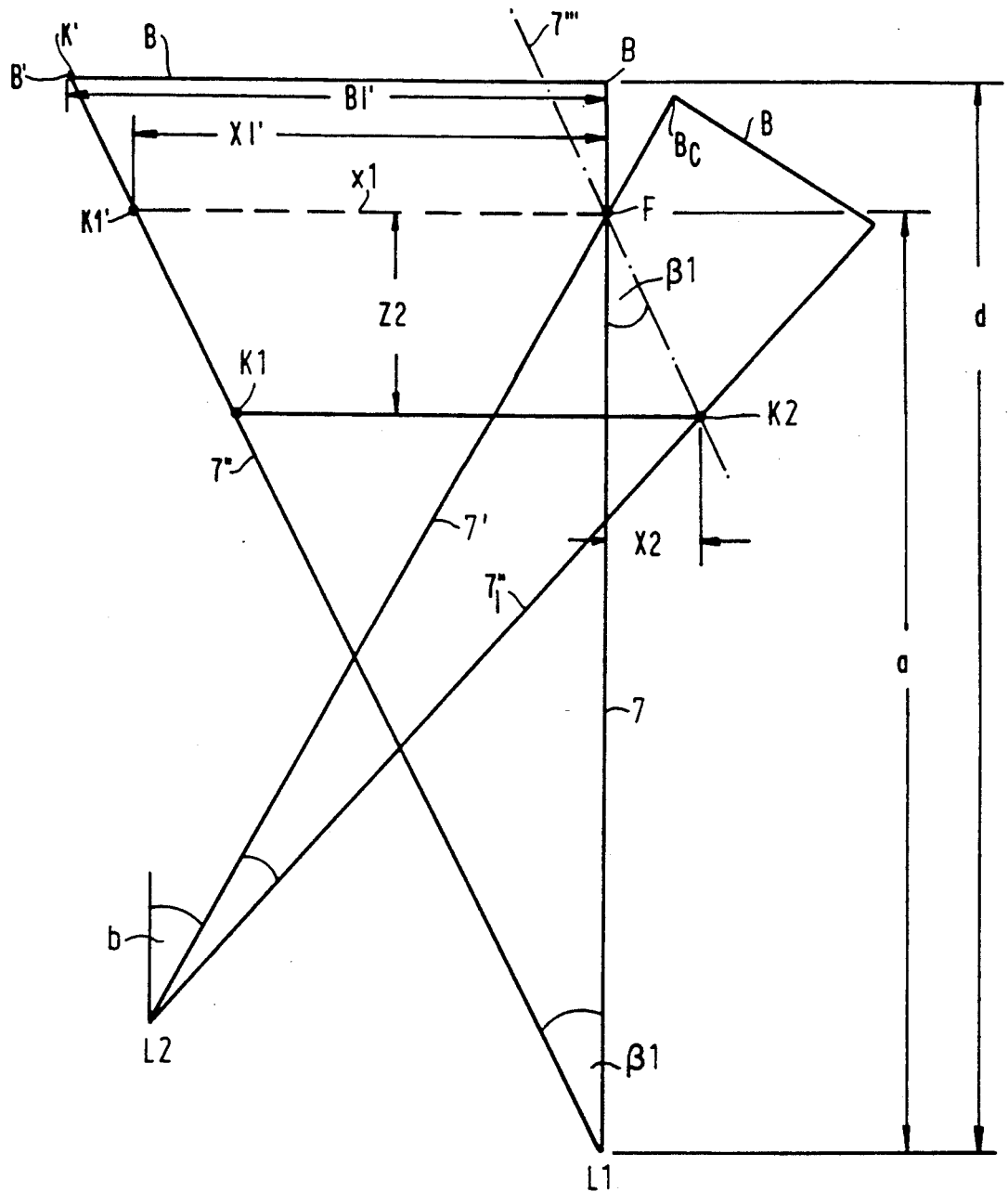
FIG. 3 shows the geometrical relationships before and after the positioning operations.

FIG. 3 shows the geometrical relationships in the X-ray images, be it that the angle of aperture of the X-ray beam is shown to be substantially larger than is possible in the device shown in FIG. 1. The position of the X-ray source during the first X-ray exposure is denoted by the reference L1. K1 denotes the position of the concrement K prior to the positioning operation. B1 denotes a point on the plane of screen B of the image intensifier. The entrance screen is a relatively large area. This area is represented by a straight line only in the region between the entrance screen center and the projection K1 of the concrement K1. The distance X1' between the focus F and the projection K1 of the concrement K1 is measured on a plane X1 extending perpendicularly to the central ray 7 and through the focus F. The angle B1 is enclosed by the X-ray beam ray 7 incident on the concrement K1 and the central ray 7.

For the first positioning operation succeeding the first X-ray exposure it is assumed that the concrement is situated in a plane which contains the focus F and which extends perpendicularly with respect to the central ray 7, and that positioning is performed so that, if the concrement were actually situated in the plane containing the focus F and extending perpendicularly with respect to the central ray, the concrement would be positioned in the focus F at the end of the positioning operation. The patient is thus displaced over the distance x1' in the x direction and accordingly in the y direction over a distance y1' which is not shown in FIG. 3. However, because the concrement K1 is situated in a plane which is situated at the distance z2 from the plane x1, the displacement in the x-direction (and the y-direction) is too large, so that the concrement will not be situated on the central ray 7 at the end of the first positioning operation. The position of the concrement at the end of the first positioning operation and prior to the second X-ray exposure is denoted by the reference K2 in FIG. 3. The distance between K1 and K2 amounts to distance x1'.

In order to check that the concrement occupies the desired position at the end of the first exposure, the cross-hairs 12 in the X-ray image on the monitor 11 are shifted by the signals u and v simultaneously with and in proportion to the displacement of the table top. The following relationship then exists between x and y and u and v:

$$x = a \cdot c \cdot u / d \tag{1}$$

$$y = a \cdot c \cdot v / d \tag{2}$$

Therein, a is the distance between F and L1, d is the distance between the radiation source L1 and the entrance plane of entrance screen B of the image intensifier, and c is a proportionality factor, which represents the quotient between 1) of the distance between a point B' on the entrance plane of the image center $B_c$ of the intensifier 5 and the image intensifier entrance and 2) the value of the signal u or v which is required for making the cross-hairs 12 coincide with the image of this point on the monitor. In other words, c is a correction factor for centering the cross hair positions on the intensifier entrance at point $B_c$. Assuming ray 7 is at the center $B_c$ of the intensifier 5, then C has a value $B1'/\mu$ for the x component of point B' or $B1''/v$, where $B1''$ (not shown in the Figure) represents the y component of point B' from the center $B_c$.

In accordance with the equations (1) and (2) the control unit 13 thus forms the signals x and y from the signals u and v supplied by the coordinate generator 14. When the concrement has reached the position denoted by the reference K2 in FIG. 3, the concrement K and the cross-hairs 12 coincide on the monitor, even though the concrement K2 is not situated on the central ray 7 as appears from FIG. 3. The values x1' and y1' which are supplied by the position detectors Px and Py at the end of the positioning operation are stored in the control unit 13.

As appears from FIG. 3, at the end of the first positioning operation the concrement K2 is situated at a distance x2 from the focus F in the x direction and at the distance z2 from focus F in the z direction. Because the connecting line 7''' between K2 and F has the same direction as the connecting line between L1 and K1, the angle between the connecting lines F-K2 and the central ray corresponds to the angle $\beta 1$; $\beta 1$ is $$\beta 1 = \arctan(x1'/a) \tag{3}$$

For a point on the connecting line F-K2 the equations $$x = z \cdot x'/a \tag{4}$$

and $$y = z \cdot y'/a \tag{5}$$

are applicable.

In accordance with the equations (4) and (5) the concrement is shifted along a straight line 7''' through the focus F when the coordinates x, y and z relate as defined by the equations (4) and (5). Thus, it is only necessary to recognize when the concrement F is situated exactly in the focus, so that the shift can be terminated.

This is realized by means of a second X-ray image for which the X-ray imaging device is pivoted through an angle b of, for example 40°. Angle b must be larger than half the angle of aperture in order to ensure that the radiation beam completely covers the entrance planes of the image intensifier. The second X-ray image is stored in the digital image memory 10 and is displayed on the monitor 11, u and v being preset so that the cross-hairs 12 again occupy their original position (image center). Subsequently, the second positioning operation is performed, the table top being displaced in all three directions until the cross-hairs 12 and the image of the concrement on the monitor coincide.

It can be demonstrated that the cross-hairs on the monitor coincide with the image of the concrement and that at the same time the concrement reaches the focus when the following conditions are satisfied:

1. The values x and y are modified in dependence on z in accordance with the equations (4) and (5). This means that x and y are also modified relatively to one another in a well-defined ratio (x1'/y1'). The resultant shifts for the x direction for the second operation and the y direction must be made in addition to the shifts already performed during the first positioning operation. Consequently, during the second positioning operation the values x1' and y1' must be added to the values calculated according to the equations (4) and (5), for the first operation respectively, in order to calculate the desired values for the x position and the y position for the second positioning operation.

2. The same relationship exists between v and u as between y and x, i.e. the following equation holds good:

$$v = u \cdot y1'/x1' \tag{6}$$

3. The variables z and u, determining the table top displacement (x, y, z) in accordance with the equations (4) and (5) and the shift of the cross-hairs (u, v) in accordance with the equation (6), relate in accordance with the following equation:

$$z = u \cdot A / (B + u \cdot D) \tag{7}$$

Therein, A, B and D are constants which are determined by the imaging device, i.e. by the values a, c and d, the pivot angle b and the angle $\beta 1$, during the first X-ray exposure in accordance with the equations $$A = a \cdot c \cdot \cos(\beta 1) \tag{8}$$

$$B = d \cdot \sin(b + \beta 1) \tag{9}$$

$$D = c \cdot \cos(b + \beta 1) \tag{10}$$

The pivot angle b is either known in advance when the X-ray imaging system 5, 6 is pivoted each time to an accurately defined angular position, or is measured by means of a suitable angle detector which is coupled to the supporting arm 8. The angle $\beta 1$ results from the value x1' measured and stored after the first exposure in accordance with the equation (3).

In accordance with the above conditions, u and v can no longer be independently selected for the second positioning operation. Consequently, for the second positioning operation v is not directly present via the generator 14 but is calculated from the value u by the control unit 13 in accordance with the equation (6). This different formation of v during the two positioning operations is diagrammatically represented by a switching unit 15 which connects one control input of the monitor to the output of the generator 14 during the first positioning operation and connects this input to an output of the control unit 13 during the second positioning operation. From the value u the control unit 13 also calculates the value z in accordance with the equation (7) or the values x and y.

The calculation can be step-wise performed during the second positioning operation so that in each position the associated values of u, v, z, x, and y are calcuated for the next shifting step of the cross-hairs and the table top. This implies that the control unit 13 must perform these calculations at a corresponding speed. However, it is in principle also possible to calculate and store the associated pairs of values for all steps already after the first positioning operation, and to fetch the paris of values stored for the relevant position during the second positioning operation. However, this necessitates a correspondingly large storage capacity of the control unit 13.

Instead of calculating the value z from u it is also possible to calculate the value u from z. In accordance with the equation (7) this is possible only by way of a digital iteration method, but the execution of such a method is not problematic when use is jade of a suitable constructed control unit (microprocessor). In this case the operator presets the table top displacement in the z-direction via a suitably constructed control unit and all other values (x, y, u and v) are derived therefrom so that the operator can thus directly determine the speed of displacement.

For the example whose geometry is shown in FIG. 3 it was assumed that the concrement was situated below the plane X1 defined by the focus F. In such a case the concrement is imaged to the left of the cross-hairs in one X-ray image and to the right of the cross-hairs 12 in the other X-ray image. Consequently, the sign of u is reversed during the positioning operations. However, if the concrement were situated above F, i.,e. between the parallel planes defined by the image intensifier entrance plane through B and plane X1 through the focus F, the concrement would be imaged on the same side of the cross-hairs also after the second X-ray exposure. In this case u should be varied in the same direction during the two positioning operations. On the other hand, in the latter case z should ve varied in the opposite direction in comparison with the situation where the concrement is situated underneath F. The sign of the displacement of the table top in the z direction, therefore, can be unambiguously derived from the variation of u during the first positioning operation (or from the sign of x1) and the sign of u during the second positioning operation.

So as not to endanger the patient during the pivoting of the image intensifier in the position for the second X-ray exposure, the distance between the image intensifier 5 and the focus F can be increased by shifting the image intensifier in the longitudinal direction of the supporting arm 8. In such a case the constants A, B and D in the equation (7) must be adapted to the changed geometry.

The operation of the control unit 13 is digital; the D/A or A/D converters which are possibly required and via which this unit cooperates with the other units are not shown in FIG. 2. Preferably, the control unit is realized by means of a microprocessor which controls the positioning operations in accordance with a suitable program. In that case the changing of the generating of the signal v during the second positioning operation, performed by a switching device 15 in FIG. 2, can be realized on the basis of software. The microprocessor may also perform the function of the controllers Rxy and Rz.

The method described above was performed so that the X-ray imaging system was pivoted through a given angle after the first X-ray exposure, so that different relative orientations occur during the two X-ray exposures. Considering that the concrement is also imaged from different orientations because of the patient displacement prior to the second X-ray exposure, it will be apparent that the pivoting of the X-ray imaging system is not absolutely necessary per se in order to obtain different relative orientations.

Therefore, the second X-ray exposure can also be performed with the same direction of the central ray, i.e. the X-ray imaging system need not be pivotable. In order to obtain different orientations, when the central ray already happens to pass through the concrement during the first exposure, the table top must be additionally displaced over a defined distance relative to the central ray, or vice versa, after the first positioning operation and before the second X-ray exposure. This additional displacement must be neutralized again during the second positioning operation (after the second exposure). The simple relationships in accordance with the equations (1) and (2) again hold good. However, because the differences in the orientations are smaller than when the X-ray imaging system is pivoted, the positioning accuracy that can be achieved by means of this embodiment is lower.

I claim:

1. Apparatus for positioning a patient on a table top compprising:
   means for forming a first x-ray image from a first orientation relative to the table top;
   means for electronically storing the first image;
   means for displacing the table top in first and second orthogonal directions during a first positioning operation;
   means for superimposing an electronic marker over the first image, the marker and image being shifted relative to one another and in accordance with the magnitude of displacement of said first operation;
   means for forming a second X-ray image from a second orientation relative to the table top;
   means for electronically storing the second image;
   means for displacing the table top in the first and second directions and in a third direction orthogonal to the first and second directions during a second positioning operation;
   means for automatically linking the displacement in the third direction the displacements in the first and second directions of the first operation wherein the magnitude of displacement in the first and second directions of the second operation is proportional to the product of the magnitude of displacement in the third direction with the magnitude of displacement in the first and the second directions of the first positioning operation;
   means for calculating the relationship between the relative shift in displacement of the marker and the table top from the magnitudes of displacement of the table top after forming the first image; and
   means for displacing the table top in accordance with said calculations.

2. The apparatus of claim 1 wherein said means for forming said first and second images includes X-ray means having a given central ray such that the first and second orientations include maintaining said central ray in relative fixed position.

3. The apparatus of claim 1 wherein said means for forming said first and second images inlcudes X-ray means having a given central ray and means for pivoting the X-ray means from a first to a second position corresponding respectively to said first and second orientations.

4. The apparatus of claim 3 wherein said means for displacing displaces said table relative to a reference point, said X-ray means comprising an X-ray image intensifier and an X-ray source for directin rays on the intensifier, said X-ray means being pivotable about a pivot defining said reference point.

5. An appartaus as claimed in claim 4, further comprising a shockwave generator (1) having a focus at said point.

6. A method of positioning a patient on a table top comprising:
   forming a first X-ray image from a first orientation relative to the table top;
   electronically storing the first image;
   displacing the table top in first and second orthogonal directions during a first positioning operation;
   superimposing an electronic marker over the first image, the marker and image being shiafted relative to one another in accordance with the magnitude of displacement of said first operation relative to the table top;
   forming a second X-ray image from a second orientation relative to the table top;
   electronically storing the second image;
   displacing the table top in the first and second directions and in a third direction orthogonal to the first and second directions during a second positioning operation;
   automatically linking the displacement in the third direction to the displacements in the first and second directions of the first operation wherein the magnitude of displacement in the first and second directions of said second operation is proportional to the product of the magnitude of displacement in the third direction with the matnitude of displacement in the first and in the second directions of the first positioning operation;
   calculating the relationship between the relative shaft in displacement of the marker and the table top from the magnitudes of displacement of the table top after forming the first image; and
   displacing the table top in accordance with said calculations.

7. A method as claimed in claim 6 wherein the first and the second images are formed with a central ray extending in different directions.

8. A method as claimed in claim 6 wherein the images are formed with x-rays having a central ray, the first and second x-ray images are formed using the same position and direction of the central ray, the table top being displaced over a defined distance in the frist and the second directions after the first positioning operation and before forming the second image.

* * * * *